United States Patent
Izvoztchikov et al.

(10) Patent No.: US 7,568,514 B2
(45) Date of Patent: Aug. 4, 2009

(54) DEVICE FOR MOUNTING HISTOLOGICAL AND BIOLOGICAL SPECIMENS

(76) Inventors: Ilia Borisovitch Izvoztchikov, ul.Jaka Duklo, d.8 korp 2, kv. 18, 194223 St. Petersburg (RU); Anatoly Ivanovitch Kurapov, pr.Lunacharskogo, d.80 korp. 4, kv. 135, 195274 St. Petersburg (RU)

( * ) Notice: Subject to any disclaimer, the term of this patent is extended or adjusted under 35 U.S.C. 154(b) by 889 days.

(21) Appl. No.: 10/546,428

(22) PCT Filed: Feb. 18, 2004

(86) PCT No.: PCT/RU2004/000063

§ 371 (c)(1),
(2), (4) Date: Aug. 19, 2005

(87) PCT Pub. No.: WO2004/077051

PCT Pub. Date: Sep. 10, 2004

(65) Prior Publication Data
US 2006/0077498 A1    Apr. 13, 2006

(30) Foreign Application Priority Data
Feb. 27, 2003    (RU)    .............................. 2003106457

(51) Int. Cl.
*B32B 37/18*    (2006.01)
(52) U.S. Cl. ........................... 156/571; 156/99; 156/570
(58) Field of Classification Search .................. 156/99, 156/556, 566, 567, 568, 569, 570, 571
See application file for complete search history.

(56) References Cited
U.S. PATENT DOCUMENTS

| | | | | |
|---|---|---|---|---|
| 3,450,591 A | * | 6/1969 | Zodrow ....................... | 156/571 |
| 3,735,731 A | * | 5/1973 | Tavernier .................... | 118/220 |
| 3,869,331 A | * | 3/1975 | Saso ........................... | 156/571 |
| 3,891,327 A |   | 6/1975 | Grace | |
| 4,171,241 A | * | 10/1979 | Henderson et al. .......... | 156/556 |
| 4,428,793 A |   | 1/1984 | Sato | |
| 5,190,612 A | * | 3/1993 | Orlandi ....................... | 156/567 |
| 5,580,414 A | * | 12/1996 | Ljungmann ................. | 156/363 |
| 5,733,410 A | * | 3/1998 | Gore et al. .................. | 156/556 |
| 5,989,386 A |   | 11/1999 | Elliott | |
| 6,302,985 B1 |   | 10/2001 | Takahashi et al. | |
| 6,382,693 B1 | * | 5/2002 | Ljungmann ................. | 294/64.1 |
| 6,474,386 B2 |   | 11/2002 | Takahashi | |
| 6,521,186 B1 | * | 2/2003 | Izvoztchikov et al. ........ | 422/99 |
| 6,796,353 B2 | * | 9/2004 | Lang et al. .................. | 156/556 |

FOREIGN PATENT DOCUMENTS

| | | |
|---|---|---|
| EP | 105 2497 | 1/2003 |
| JP | 112 02 215 | 7/1999 |
| RU | 214 8952 | 5/2000 |

* cited by examiner

*Primary Examiner*—Mark A Osele
(74) *Attorney, Agent, or Firm*—Paul Vincent

(57) ABSTRACT

The inventive device for enclosing histological and biological samples comprises a platform for an object glass and means for placing a cover glass thereto. Said means for placing the cover glass is embodied in the form of a comb arranged above the platform and provided with a mechanism for a pendulous (the first embodiment of the device) or reciprocating (the second embodiment of the device) motion above said platform. The platform is limited by a vertical arrest which is arranged on the side of the means for placing a cover glass and provided with slots for accommodating the comb teeth therein. In addition, said device can be provided with a rolling press arranged above the comb.

4 Claims, 5 Drawing Sheets

DEVICE FOR MOUNTING HISTOLOGICAL AND BIOLOGICAL SPECIMENS

This application is the national stage of PCT/RU2004/000063 filed on Feb. 18, 2004 and claims Paris Convention priority of RU 200 310 6457 filed Feb. 27, 2003.

BACKGROUND OF THE INVENTION.

This invention relates to a field of medicine, in particular to diagnostic instruments, and more precisely to devices for mounting histological and biological specimens in an optical medium for subsequent microscopic examination.

The prepared and stained histological and biological specimens are placed in special mounting media to create an optically homogeneous medium and to ensure that the specimens will remain intact for the duration of the examination. The mounting media used include Cedar oil, cedax or polystyrene, for example.

Specimens are often mounted manually. To do this, the specimen is placed on a object slide, a drop of a xylene solution of the above mentioned medium is added and a cover glass is carefully positioned on the specimen. (Roskin G. I., Microscopic Technique, "Sovetskaya Nauka" State Publishing House, Moscow 1951, p. 152; Merkulov G. A., A Brief Introduction to Pathohistological Technique, "Medgis", Leningrad 1951, p. 86; Romeis B., Microscopic Technique, "IL", Moscow 1953, pp. 191-192.) Another method consists of placing a drop of a resin dissolved in xylene on an appropriately sized cover glass and then carefully lowering the object slide with the specimen on it until the specimen makes contact with the drop of solution on the cover glass (Lilli R., Technique of Pathology and Practical Histochemistry, "Mir", Moscow 1969, p. 85).

It is mentioned in all sources that manually applying cover glasses may cause air bubbles to form beneath the cover glass which distort the microscopic image. These bubbles can be removed by carefully applying pressure to the cover glass with the tip of a dissecting needle. B. Romeis, however, points out that "the specimen is usually damaged" by such a procedure. Moreover, manually applying cover glasses is labor- and time-consuming, hardly efficient and can only be performed by trained personnel with appropriate experience.

The Consul Automatic Coverslipper manufactured by the English company Shandon Life Sciences International Ltd. (Shandon Consul Automatic Coverslipper) is already known. It comprises a cover glass magazine with a pusher, a object slide holder, a mounting medium dispenser and a roller device.

The object slide slide holder consists of a plurality of semi-frames that are attached to a bar and are mounted so as to pivot perpendicularly thereto. In its initial position, the roller device of the Consul Automatic Coverslipper consists of a table and two rollers that are located beneath the cover glass. The table together with the rollers is adapted to be moved perpendicular to the surface of the cover glass. The rollers may be diverted by spring-biased connecting rods.

The object slides are placed on the bar which is adapted to be moved vertically. The object slides are then supplied to the work area with the help of a pivoting device. The object slide magazine and the dispenser are mounted on the frame.

The Consul Automatic Coverslipper operates as follows.

The object slide pusher moves along guideways, thus transporting the lowermost cover glass from the magazine to the work area. One dose of the mounting medium is dropped onto the cover glass from above. The pivoting device pivots the semi-frame together with the object slide into the work area and positions the object slide above the cover glass with the specimen being located on the underside. The table of the roller unit rises, thus bringing the cover glass into approximation with the object slide. The pusher of the roller unit raises the rollers until these make contact with the cover glass, whereupon the spring-biased connecting rods begin to diverge and the rollers roll over the surface of the cover glass. Hence, the center portion of the cover glass is pressed by the table, whereas the side portions are rolled by the rollers. The roller unit eventually lowers and disengages the cover glass, while the pivoting device moves the semi-frames with the mounted object slide into the initial position.

The Consul Automatic Coverslipper is capable of mounting as many as 400 specimens per hour. By virtue of this high output, it can be used successfully in pathohistological laboratories.

The disadvantages of the Consul Automatic Coverslipper are that cover glass and object slide are held horizontally during pressing and this makes it difficult to remove air bubbles from the mounting medium.

A coverslipping device is also known according to U.S. Pat. No. 4,428,793, IPK B65C 9/08, published on Jan. 31, 1984, which comprises a cover glass magazine, a table for receiving the object slide and a device for removing the cover glass from the magazine, transporting it to the object slide table and applying it to the object slide. This device consists of a holder provided with a suction cup and a spring-loaded pusher, the suction cup being located above the pusher. The holder is lowered into the cover glass magazine until the suction cup engages a cover glass. The spring of the pusher is compressed until the pusher is level with the suction cup. Once the cover glass has been removed from the magazine, the pusher spring expands and pushes one end of the cover glass downwards. While it is being transported to the object slide table, the cover glass is slightly inclined owing to the difference in the levels of the suction cup and the pusher. The holder lowers the cover glass with its lower end onto the edge of the object slide at which a drop or smear of the mounting medium is located. While the cover glass is being lowered, the pusher presses against it. The pusher spring is compressed until the suction and pusher are horizontal—only then is the suction cup disengaged from the cover glass. Hence, the cover glass is first placed on the object slide gradually and at a specific angle, thereby allowing air bubbles to be eliminated from the medium more easily.

The disadvantage of this device is that it is difficult to remove an individual cover glass with a thickness of maximum 0.06-0.25 mm from the stack in the cover glass magazine, all the more so since the spring force of the pusher acts on the cover glass stack every time a cover glass is removed. In addition, when applying the cover glass, the force required to compress the spring may cause the specimen to be damaged.

The device for removing and applying cover glasses in accordance with U.S. Pat. No. 5,989,386, IPK B32 B31/04, published on Nov. 23, 1999, comprises an application head, at one end of which there are located two suction cups at an angle to one another. Interposed between the suction cups is a spring-biased plunger capable of upward and downward movement that is driven by a solenoid. The plunger, when retracted, does not contact the cover glass. In addition, a spring-biased level is mounted at the other end of the application head opposite the suction cups and plunger.

This device operates as follows. The head is lowered into the cover glass magazine until the plunger contacts the uppermost cover glass, whereupon this is engaged by the suction cups. Owing to the spring action of the plunger and the angular positioning of the suction cups, the cover glass is bent and thus removed from the stack. The head then transports the cover glass to the object slide. The end of the cover glass located opposite the point of suction is now pushed downwards by the lever so that the cover glass is laid on the object slide at a specific angle relative to the horizontal. The head continues to move downwards until the end of the cover glass held by the suction cups rests against the object slide. The lever mounted on the application head—it is capable of moving clockwise and counterclockwise—then places the cover glass on the object slide, whereupon the suction cups are released.

The apparatus described in U.S. Pat. No. 5,989,386 is supposed to remove "a large percentage of individual cover glasses". In practice, however, the apparatus is not always successful in removing an individual cover glass by means of the suction cups. Consequently, the cover glass must be ejected from the magazine by other devices before they can be successfully engaged by the suction cups. The use of a spring-biased plunger in addition to a lever may also cause damage to the specimen, exactly as in the case of the device according to U.S. Pat. No. 4,428,793.

The apparatus for mounting histological specimens in accordance with U.S. Pat. No. 6,474,386, IPK B65H29/24, published on Nov. 5, 2002, makes it possible to reliably remove the air from the space between the cover glass and object slide. This apparatus contains a platform for the object slide as well as a means for picking up a cover glass by suction and positioning it on the object slide in an angular fashion. This suction and positioning means comprises a cylinder mounted on a stand next to the platform and capable of upward and downward movement by means of a motor. This cylinder also has mounted on it a holder arm provided with its own motor and capable of clockwise and counterclockwise rotation. The free end of the holder arm has a suction cup connected to a vacuum pump. The holder arm can raise and lower the suction cup until the cover glass to be transported is located in a horizontal position.

The apparatus according to U.S. Pat. No. 6,474,386 operates as follows.

A object slide with a specimen and a drop of mounting medium is placed on the platform. The suction means picks up the cover glass with the help of the suction cup at one end and positions it above the object slide such that the engaged end is higher than the free end. The cylinder now moves downwards until the horizontal axis of the holder arm mount is located below the object slide on the platform. In this position, the lower end of the cover glass contacts the edge of the object slide at an acute angle to the horizontal. The motor-driven holder arm now rotates counterclockwise, whereupon the cover glass held by the suction cup is gradually lowered onto the object slide. The suction cup is then disengaged. It is claimed that the apparatus is capable of mounting histological specimens without damage.

The drawback of the cited apparatus lies in how the cover glass is picked up by means of the suction cup. This construction requires a vacuum pump as well as a complicated control unit, thus increasing both the weight of the apparatus as well as the cost of manufacturing it.

SUMMARY OF THE INVENTION

The invention as set forth in this application proceeds from the technical task of developing a simpler and more reasonably priced apparatus—with respect to both the manufacture and operation thereof.

At the same time, another objective of the invention was to do without suction cups for removing the cover glasses from a stack and transporting them to the object slide.

In accordance with the invention, this is achieved by a device for mounting histological and biological specimens that comprises a platform for the object slide and a means for applying a cover glass to the object slide in the form of a comb which is located above said platform and is equipped with a mechanism for executing a pendulous or reciprocating movement above said platform. On the side of the positioning means, the platform is delimited by a vertical stop having a plurality of slots which mesh with the teeth of said comb.

The device in accordance with the invention may also be equipped with a roller press which is connected to the drive means for moving said comb and is located above the comb. This mechanism can be constructed in the form of a cylindrical segment or a roller.

If the movement of the comb above the platform is pendulous, the roller press may be constructed as a cylindrical segment. However, if the comb executes a reciprocating movement above the platform, the roller press can be constructed as a roller. Other forms of presses are also possible.

BRIEF DESCRIPTION OF THE DRAWING

The invention is described hereinbelow by way of example with reference to the accompanying drawings 1 to 5(a-d), in which.

DESCRIPTION OF THE PREFERRED EMBODIMENT

Figure 1:
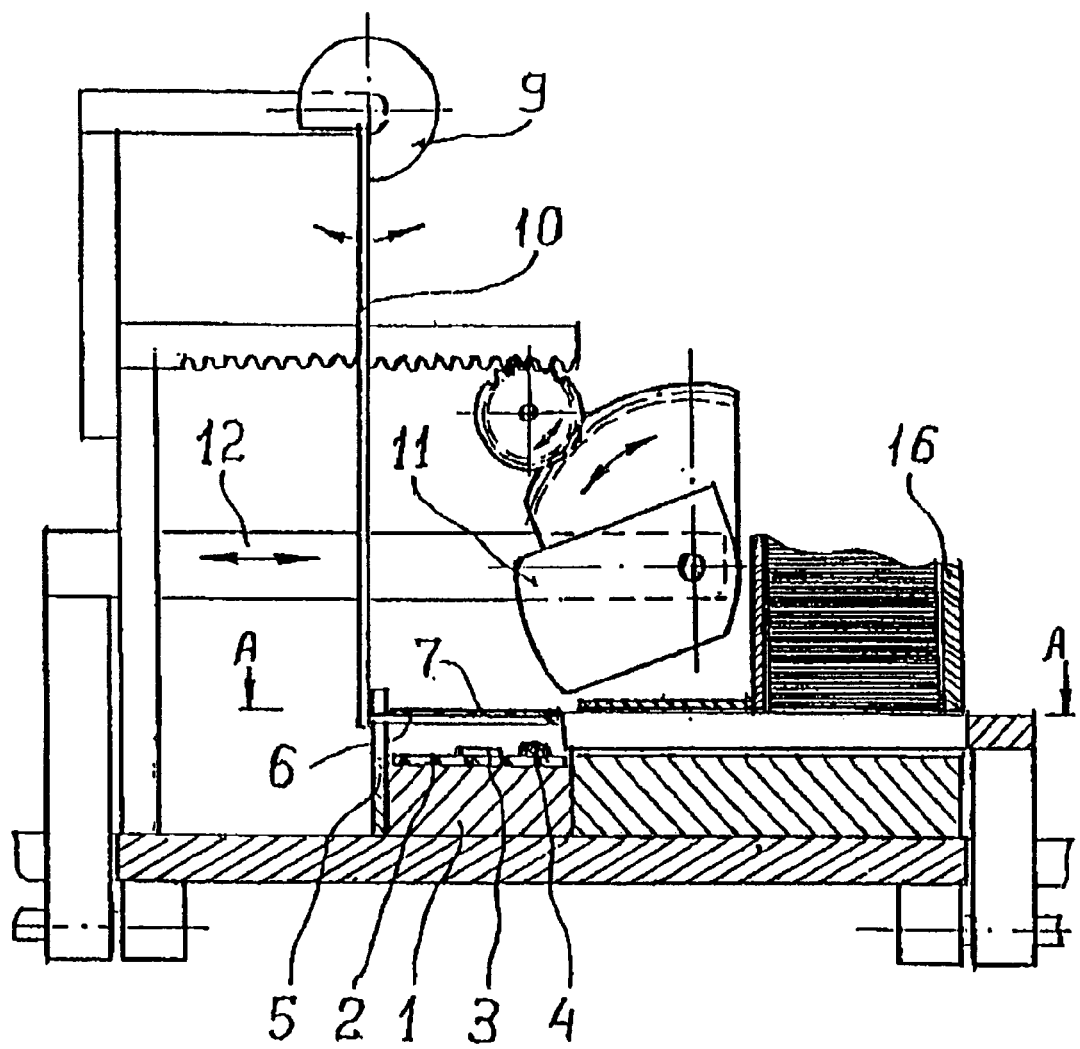
FIG. 1 shows the device in accordance with the invention, the movement of the application means above the object slide platform being pendulous.
Figure 3:
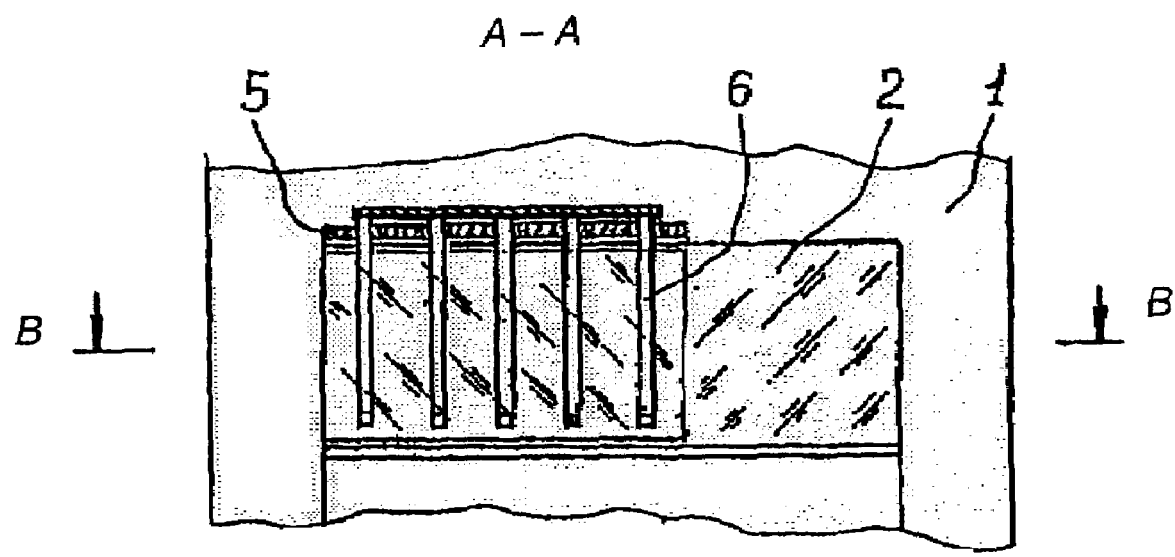
FIG. 3 shows the object slide platform and the application means (the comb) in a top elevation.
Figure 4:
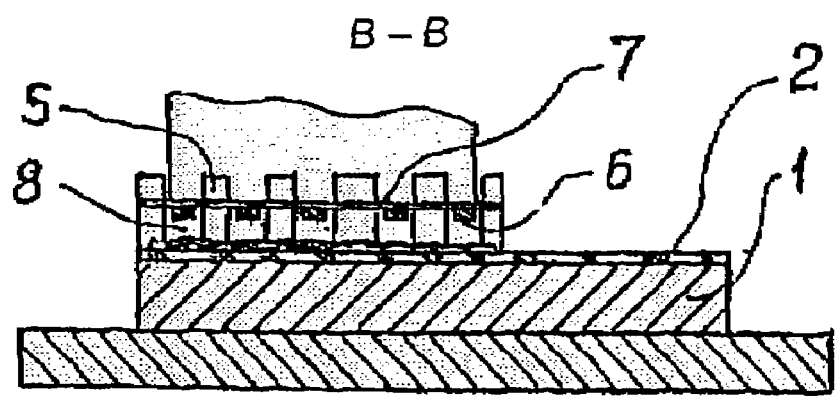
FIG. 4 shows a cross section along line B-B through the part of the device in accordance with the invention as illustrated in FIG. 3.

On platform 1 (FIGS. 1 and 2) there is mounted a object slide 2 together with a histological specimen 3 (FIG. 1) and a drop (smear) of mounting medium 4. Platform 1 is limited by stop 5 on one side. A means 6 for applying the cover glass 7 is located above platform 1 and object slide 2. The application means 6 is embodied as a comb (see FIG. 3) whose teeth 6 mesh with the slots 8 of stop 5 (FIG. 4). The teeth of comb 6 are at the same level; they may be needle-shaped or lamellar-shaped. In a first embodiment of the invention, comb 6 is connected to the mechanism for pendulous movement 9 via a bar 10. The roller press 11, whose width corresponds to the length of the cover glass, is located above comb 6 and cover glass 7 and is connected to the mechanism for pendulous movement 9 by a linkage 12 (FIG. 1).

Figure 2:
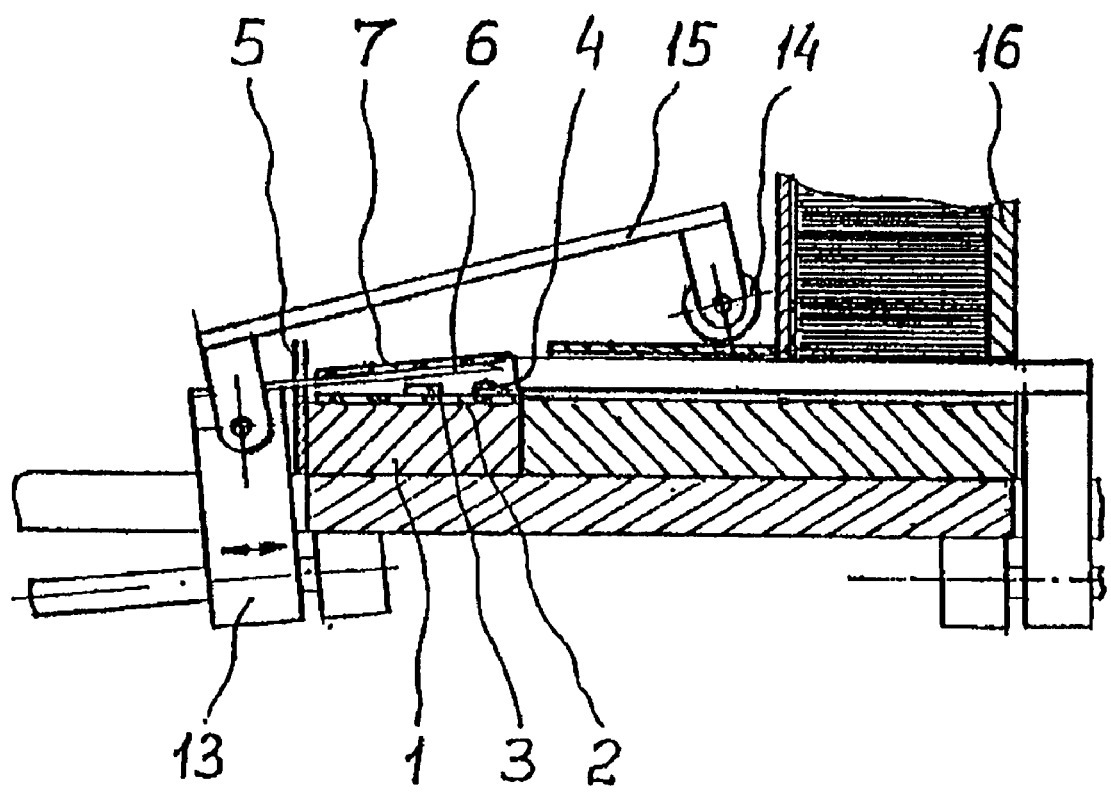
FIG. 2 shows the device in accordance with the invention, the application means above the object slide platform executing a reciprocating movement.

In a second embodiment of the invention shown in FIG. 2, comb 6 is connected to a mechanism 13 which makes a reciprocating movement over the object slide possible. The roller press is constructed as a roller 14. The length of said roller press corresponds to the length of the cover glass and it is connected to mechanism 13 via bar 15. Roller 14 is located above comb 6 with cover glass 7.

The device is also equipped with a cover glass magazine 16. The cover glasses on comb 6 are supplied with the help of a special pusher that moves through a slot 5 (not shown) in the lower portion of cover glass magazine 16. This slot is higher than one cover glass, but lower than two cover glasses.

The device operates as described below.

The object slide 2 on which is located the histological specimen 3 and a drop of mounting medium 4 is placed on platform 1. A cover glass 7 is transported on comb 6 out of the cover glass magazine 16. The cover glass is applied to the object slide differently depending on the embodiments of the invention. What all embodiments have in common, however, is the fact that the cover glass is lowered onto the object slide at a specific angle beginning with the side on which the drop of mounting medium is located. The application operation is effected by gradually withdrawing the comb from the space between the cover glass and object slide.

Figure 5A:
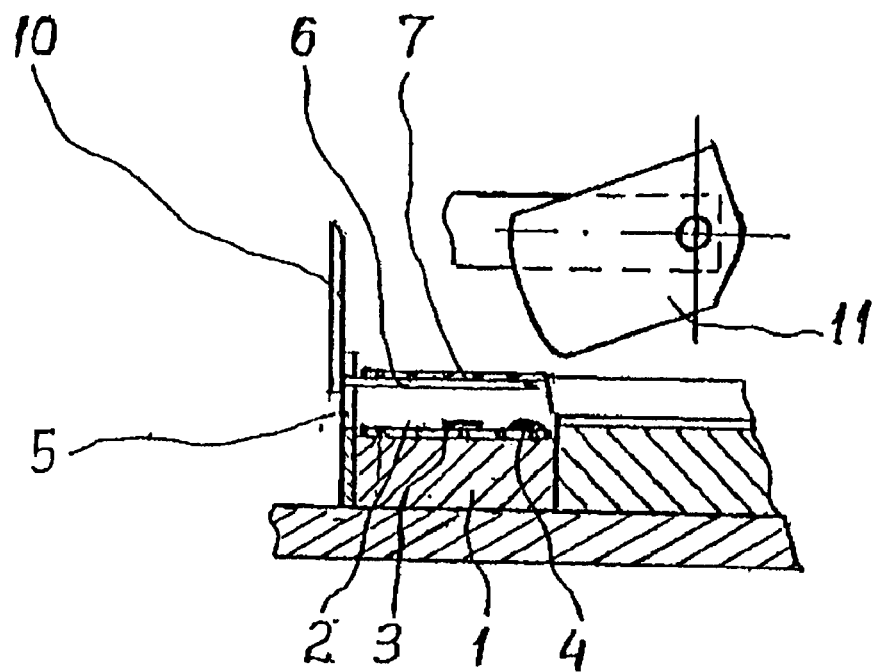
FIGS. 5a to 5d are schematic illustrations showing stages in the course of applying a cover glass to a object slide with a specimen.
Figure 5B:
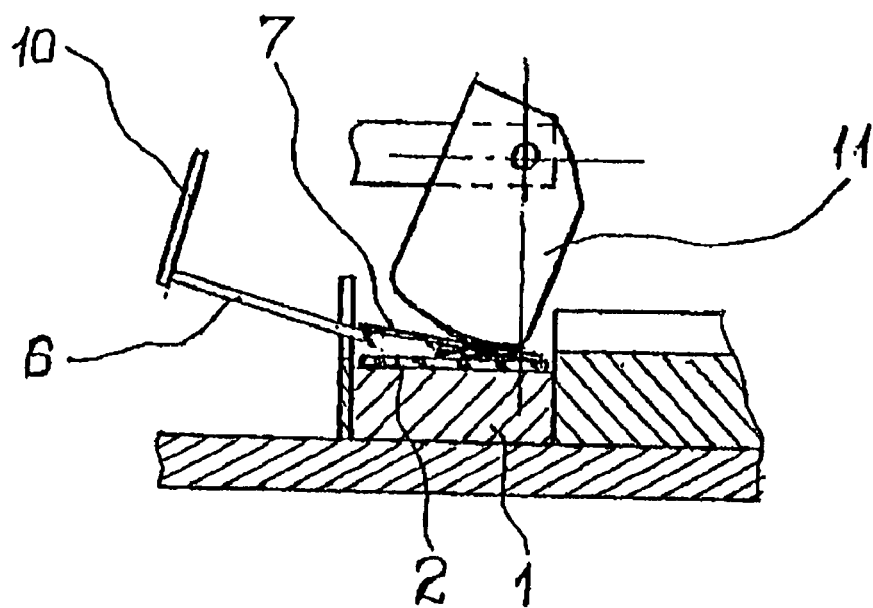
Figure 5C:
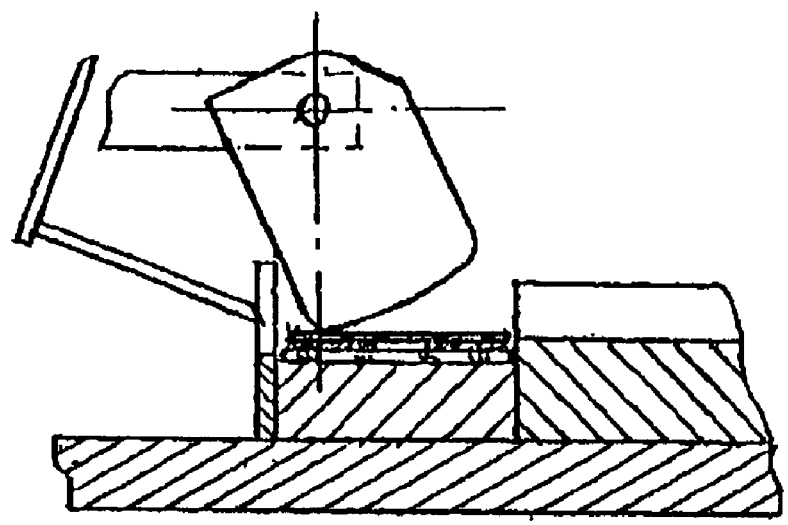
Figure 5D:
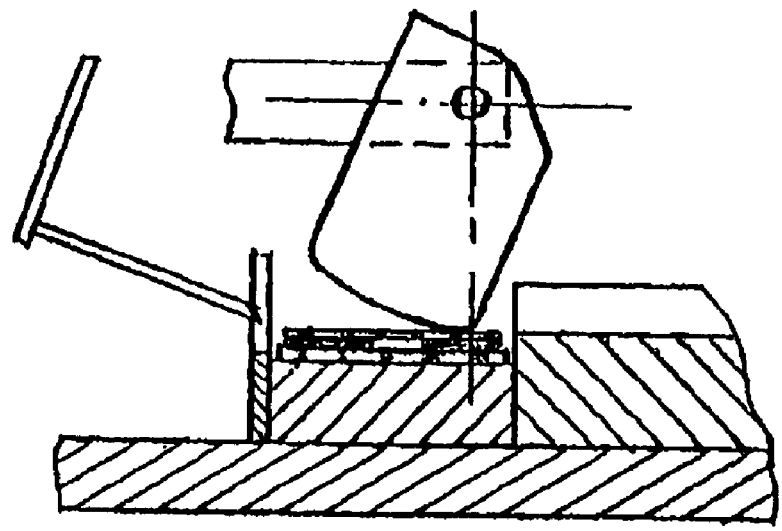

The application operation is illustrated schematically in FIGS. 5*a*-5*d* for the first embodiment of the device. FIG. 5*a* shows the initial position in which cover glass 7 rests on comb 6; stop 5 prevents cover glass 7 from sliding off the platform. The mechanism for pendulous movement 9 begins to pull comb 6 to one side. One end of cover glass 7 is lowered onto object slide 2. While comb 6 continues to move, cover glass 7 is gradually lowered onto object slide 2 due to its inclination (see FIG. 5*b*), thus promoting the elimination of air from the space between the cover glass and slide. At the same time comb 6 is executing its pendulous movement, mechanism 9 begins to move roller press 11 via linkage 12, causing it to roll over the surface of the cover glass first in the direction of stop 5 (FIG. 5*c*) and thereafter in the opposition direction (FIG. 5*d*).

In the second embodiment of the device (FIG. 2), mechanism 13 pulls comb 6 causing cover glass 7—as in the first embodiment—to be gradually lowered onto the object slide 2 owing to its inclination. Mechanism 13 moves roller 14 via bar 15 causing the roller to roll over cover glass 7 in the direction of stop 5. The backward movement of drive 15 causes roller 14 to roll back in the opposite direction.

The movement of the roller press serves to additionally eliminate any air bubbles that might be present in the mounting medium between the cover glass and object slide. The fact that the width of the press (or the length of the roller) corresponds to the dimensions of the cover glass ensures that there is uniform weight distribution, thus preventing any damage to the specimen.

The device in accordance with the invention is sufficiently simply, requires neither pneumatic nor vacuum devices nor a suction control unit, and is also reliable in operation.

The claimed device for placing cover glasses on histological and biological specimens can be used in specialized histological laboratories, in any medical and biological laboratories as well as in institutions that are involved in examining biological tissues and cells.

We claim:

1. A device for mounting a histological or biological specimen to an object slide and for covering the specimen with a cover glass, the device comprising:
   a platform for supporting the object slide;
   a comb member for applying the cover glass to the object slide, said comb member disposed above said platform;
   means for executing a pendulous or reciprocating motion, said motion means cooperating with said comb member to position the cover glass; and
   a vertical stop delimiting a side of said platform, said vertical stop having a plurality of slots which mesh with teeth of said comb member.

2. The device for mounting histological and biological specimens of claim 1, further comprising a pressing means disposed above said comb member, said pressing means cooperating with said motion means to press upon the cover glass covering the specimen.

3. The device for mounting histological and biological specimens of claim 2, wherein said pressing means is constructed as a cylindrical segment.

4. The device for mounting histological and biological specimens of claim 2, wherein said pressing means is constructed as a roller.

* * * * *